United States Patent
Norquest et al.

(10) Patent No.: US 6,203,515 B1
(45) Date of Patent: Mar. 20, 2001

(54) INFRARED TREATED TAMPON APPLICATORS

(75) Inventors: Robert Clinton Norquest, Dover, DE (US); Suzanne E. Assenheimer Downs, Ho-Ho-Kus, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/574,536

(22) Filed: May 17, 2000

Related U.S. Application Data

(63) Continuation of application No. 09/245,732, filed on Feb. 8, 1999, now abandoned, which is a continuation-in-part of application No. 09/119,439, filed on Jul. 20, 1998, now abandoned, which is a continuation of application No. 08/788,472, filed on Jan. 28, 1997, now Pat. No. 5,782,794.

(51) Int. Cl.[7] .................................................. A61F 13/20
(52) U.S. Cl. ............................................................ 604/15
(58) Field of Search ............................ 604/11–18, 57–60

(56) References Cited

U.S. PATENT DOCUMENTS

| | | |
|---|---|---|
| 2,518,486 | 8/1950 | Mende . |
| 3,724,462 | 4/1973 | Hanke . |
| 3,882,196 | 5/1975 | Hanke . |
| 3,882,869 | 5/1975 | Hanke . |
| 3,911,917 | 10/1975 | Hanke . |
| 4,412,833 | 11/1983 | Wiegner et al. . |
| 4,508,531 | 4/1985 | Whitehead . |
| 4,900,299 | 2/1990 | Webb . |
| 5,002,526 | 3/1991 | Herring . |
| 5,317,052 | 5/1994 | Ohba et al. . |
| 5,346,468 | 9/1994 | Campion et al. . |
| 5,395,308 | 3/1995 | Fox et al. . |
| 5,782,794 | 7/1998 | Downs . |

Primary Examiner—Dennis Ruhl
(74) Attorney, Agent, or Firm—Ohlandt, Greeley, Ruggiero & Perle, LLP

(57) ABSTRACT

A tampon applicator has a barrel and a plunger telescopically mounted within the barrel. In a preferred embodiment, one or both of the barrel and plunger is made of a water dispersible material, and is exposed to a source of infrared radiation to minimize surface stickiness on initial contact with moisture. In an alternative embodiment, the barrel or plunger can be coated with a water dispersible material prior to exposure to infrared radiation.

22 Claims, 1 Drawing Sheet

INFRARED TREATED TAMPON APPLICATORS

RELATED APPLICATION

This application is a continuation application of U.S. patent application Ser. No. 09/245,732, filed Feb. 8, 1999, now abandoned, which in turn is a continuation-in-part application of U.S. patent application Ser. No. 09/119,439, filed Jul. 20, 1998, now abandoned, which in turn is a continuation of U.S. patent application Ser. No. 08/788,472, filed Jan. 28, 1997, now U.S. Pat. No. 5,782,794, which issued Jul. 21, 1998.

BACKGROUND OF THE INVENTION

1. Field Of Invention

The present invention is directed to an improved tampon applicator. More particularly, the present invention is directed to a tampon applicator having a plastic-type body or coating that has been treated. Even more particularly, the tampon applicator is either molded of a polymer resin, or coated with a polymer resin, with the outside surface of the applicator then treated with infrared radiation.

Consumers desire tampon applicators that make pledget insertion easier, more convenient and less messy. In particular, for environmental reasons as well as for convenience of disposal, consumers desire applicators, especially tampon applicators, that are both biodegradable and water-soluble. An example of a water-soluble polymer used for making flushable applicators is polyvinyl alcohol (also referred to herein as "PVOH").

However, PVOH, in particular, is known to become sticky on contact with moist surfaces or under humid conditions. Heat treatment of the PVOH applicator provides crystallization that increases water resistance, but too much heat makes PVOH unacceptably stiff and brittle.

The present invention overcomes the disadvantages described above associated with tampon applicators made from water-soluble polymers in an efficient manner, and provides tampon applicators either made from, or coated with, water-soluble polymers that are able to withstand exposure to moisture, but are not unacceptably stiff. The present invention accomplishes the foregoing by heating only the outside of the applicator with infrared radiation.

U.S. Pat. No. 5,782,794, the grandparent of the present application, discloses a novel set of plasticizers suitable for use with PVOH that, in conjunction, produce a molded product having improved stability, ease of molding, and utility for tampon applicators. The disclosure of U.S. Pat. No. 5,782,794 in its entirety is incorporated herein by reference.

2. Description of the Prior Art

Tampon applicators typically are constructed from two telescoping tubes. One tube, a barrel, encloses the pledget, and the other tube, a plunger, is used to eject the pledget out of the barrel during insertion. Thus, it is essential that the tubes telescope smoothly to facilitate ejection. Any stickiness or other adhesions between the two tubes can result in poor ejection of the pledget, which in turn can make insertion of the pledget difficult, painful, or impossible. One solution to the foregoing problem is to make the diameter of the plunger less than the diameter of the barrel. However, if the plunger is much less in diameter than the barrel to prevent sticking together, the plunger will most likely disassemble from the barrel.

Furthermore, the ability of the barrel to be inserted smoothly, without dragging on the delicate vaginal tissue, is very important not only for users comfort but also for proper insertion of the pledget. Once again, any stickiness or adhesion sites on the outer surface of the barrel will impede proper insertion.

Tampon applicators formed from certain polymer resins, when dry, have glide characteristics similar to traditional plastic tampon applicators. Thus, such polymer resin tampon applicators would be expected to have optimal qualities for insertion, minimal drag on insertion and smooth telescoping of the barrel and plunger. In addition, these polymer resin tampon applicators remain dispersible and biodegradable on disposal in water.

However, the very ability of the polymer resin tampon applicators to disperse in water also creates certain drawbacks. Water-soluble polymer resins, can become sticky on contact with moist surfaces, bodily fluids or under humid conditions. Thus, tampon applicators formed from polymer resins tend to become tacky in the very environment for which it is designed. This in turn makes insertion more difficult, since the outer tube can become gummy or tacky upon insertion. Another potential problem should such a polymer resin applicator be exposed to moisture, is that the barrel and plunger may not telescope properly. The barrel and plunger may even become glued together, requiring a much greater force to eject the tampon pledget from the applicator. Additionally, humidity from the environment can permeate the packaging used to store the polymer resin tampon applicator and, thus, cause the same problems. Humidity may even cause the applicator to stick to the wrapper.

SUMMARY OF THE INVENTION

Accordingly, it is an object of the present invention to provide a water dispersible tampon applicator that has been treated with infrared radiation to avoid or minimize adverse moisture effects on the tampon applicator.

It is another object of the present invention to provide a polymer tampon applicator that has been treated with infrared radiation so that the applicator will not become sticky or begin to biodegrade upon initial contact with moist surfaces, bodily fluids or ambient humidity.

It is a further object of the present invention to provide a cardboard tampon applicator that has been coated with a water-soluble resin and then treated with infrared radiation so that the applicator will not become sticky or begin to biodegrade upon initial contact with moist surfaces, bodily fluids or ambient humidity.

It is still a further object of the present invention to provide a polymer tampon applicator that has been treated with infrared radiation so that the outside surface is crystallized to increase water resistance, yet the applicator remains flexible and, thus, usable.

Accordingly, the present invention discloses a tampon applicator having a barrel and a plunger that is telescopically mounted within the barrel. Either or both the barrel or plunger is made of, or coated with, a water dispersible polymer. The barrel or plunger is exposed to or treated with infrared radiation to minimize surface stickiness thereof when exposed to moisture.

DESCRIPTION OF THE PREFERRED EMBODIMENTS

Figure 1:
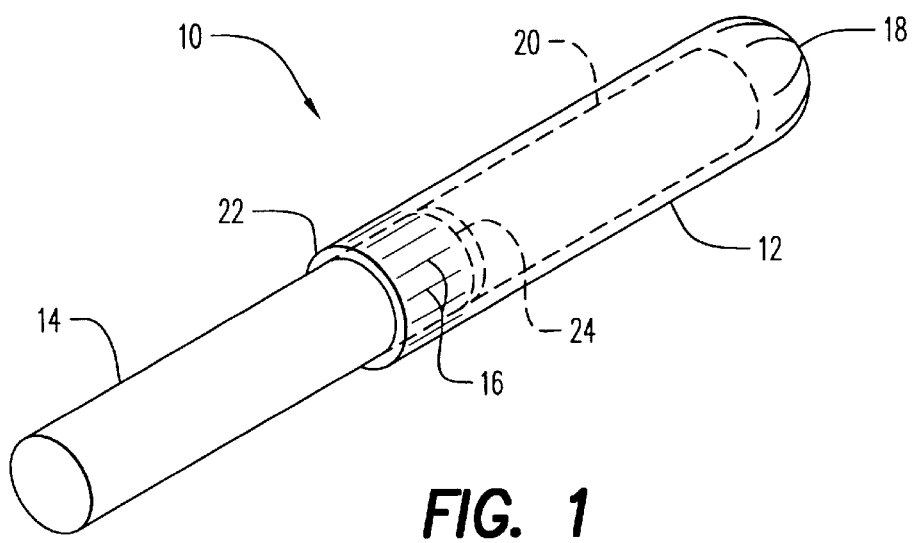
FIG. 1 is a perspective view of a tampon applicator employing a preferred method of the present invention.

Referring to the drawings and, in particular, FIG. 1, there is a tampon applicator generally represented by reference numeral 10. The applicator 10 has an outer tube or barrel 12 and an inner tube or plunger 14. The barrel 12 preferably has a curved or petal tipped end 18, and a plunger insertion end 22. The barrel 12 preferably has a plurality of fingergrips 16. The plunger 14 has an insertion end which has an edge 24. Upon assembly, pledget 20 is located within barrel 12, and plunger 14 is inserted in end 22 of the barrel. The edge 24 of plunger 14 will act against pledget 20 when the plunger is moved to eject the pledget through and out of end 18 of barrel 12.

The barrel 12 and plunger 14 can be made of any water dispersible material. Examples of suitable water dispersible polymers are microbial polyesters such as poly(b-hydroxy butyrate)("PHB"), poly(b-hydroxy butyrate)-co-(b-hydroxy valerate)("PHBV"), poly(hydroxy acids), aliphatic polyesters, polycaprolactone ("PLC"), starch, cellulose acetate and cellulose diacetate.

Alternatively, either or both the barrel 12 and plunger 14 may be made of other materials, and then coated with a water dispersible polymer. Any of the water dispersible polymers set forth above may be used as the coating for the barrel or plunger.

Although either or both the barrel and plunger may be made of, or coated with, the water dispersible polymer, it is preferable that both the barrel and plunger are either made of, or coated with, the water dispersible polymer.

In one preferred embodiment, barrel 12 and plunger 14 are made of one water-soluble polymer resin. In a second embodiment, the barrel is made of the water-soluble polymer resin, and the plunger is made of another material, such as cardboard.

Figure 2:
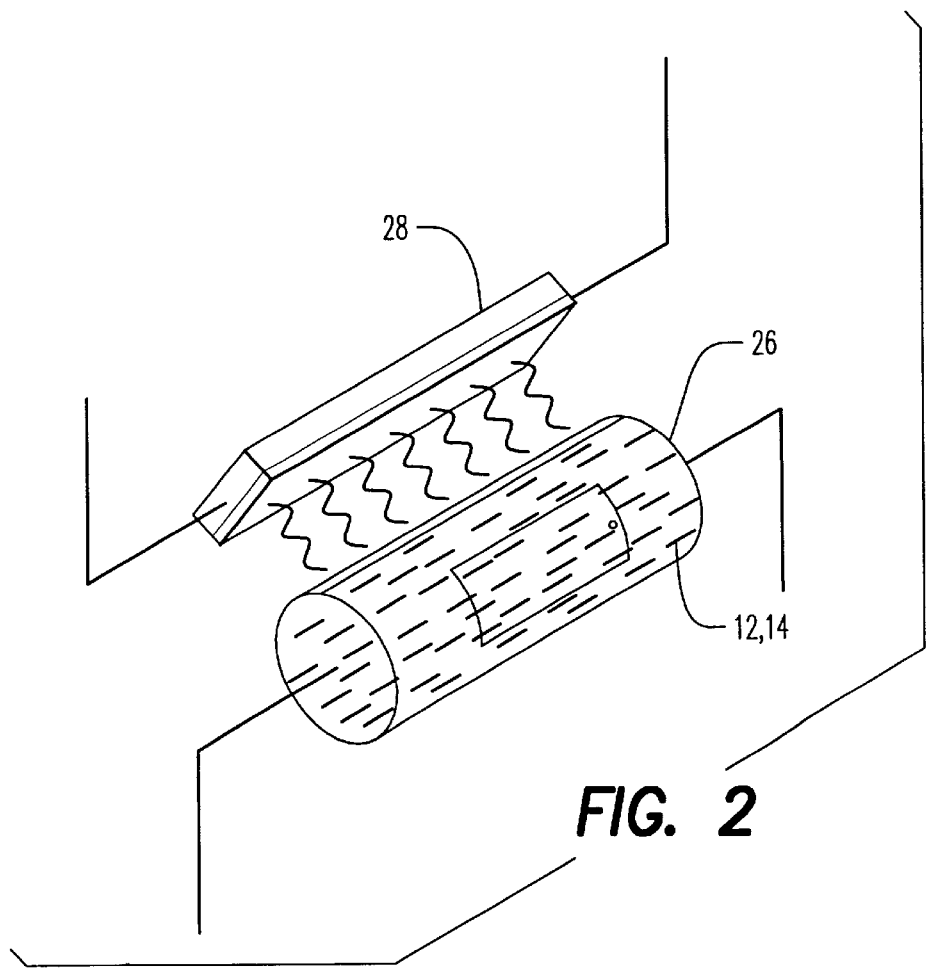
FIG. 2 is a diagram of a preferred method of treating a tampon applicator according to the present invention.

The tampon applicator assembly includes the barrel 12 and plunger 14 assembled together with the pledget 20 in the barrel. As shown in FIG. 2, the tampon applicator assembly is placed in a rotating carrier 26. The barrel 12 and plunger 14 are rotated in the rotating carrier 26 while the carrier is subjected to infrared (or "IR") radiant heater or heaters (hereinafter "IR Source") 28. As shown in FIG. 2, the heater 28 is preferably positioned approximately six inches from the carrier 26. As can be understood, the distance of the IR source 28 from the tampon applicator may be modified. However, as the distance of the IR source from the tampon applicator is modified, the temperature generated by the IR source 28 and the length of time of IR exposure will require adjustment as would be evident to those in the art.

The barrel 12 and plunger 14 are preferably treated with the IR Source 28 positioned about six inches from the carrier 26 for about five to about sixty seconds. The temperature of the IR Source is preferably from about 700° F. to about 2500° F. The effect of the IR treatment is time-temperature dependent. Thus, when the temperature of the IR Source is higher, the length of time required for IR exposure will decrease.

The temperature of the IR source 28 and the time period of IR exposure will be a function of the water-soluble polymer resin used. The polymer resin is heated to a level just below the melting point of the polymer resin. The infrared treatment affects the outer surface of the tampon applicator 10 by inducing high temperature molecular crystallinity along the backbone of the polymer resin. The polymer should not be heated to the melting point since only the cystallization of the outermost layer of the polymer resin is desired. The crystallization results in a more hydrophobic surface thereby providing a less sticky surface. However, since only the outermost layer of the polymer resin is crystallized by exposure to the IR source 28, the overall flexibility of the tampon applicator is not substantially diminished as seen with prior art methods.

Examples of melting point ranges of several polymers that may be used with the present invention are listed below in Table 1.

TABLE 1

| POLYMERS | MELTING POINT ° C. |
|---|---|
| Polycaprolactone (PCL) | 58–60 |
| Poly(b-hydroxy butyrate) | 40–180 |
| Poly (b-hydroxy butyrate)-co-(b-Hydroxy Valerate) (PHBV) | 40–180 |
| Aliphatic Polyesters | 200 |
| Cellulose Acetate (CA) | 240 |

The examples of melting points set forth in Table 1 is intended only to provide a guideline. The melting point ranges of any specific polymer is available from the manufacturer of that particular polymer.

The most preferred conditions for infrared treatment of tampon applicators made of, or coated with, PVOH are:

| | Time (seconds) | Temperature (° F.) of IR Source |
|---|---|---|
| Condition A | 40 | 1325 |
| Condition B | 20 | 1750 |

This infrared treatment does not destroy, deform or degrade the petals of the applicator. Thus, this entire tampon applicator can be treated, whereas other known treatments would affect the petals. In prior treatments, the petals required protection during treatment, i.e. only the applicator body minus the petals could be treated.

U.S. Pat. No. 5,782,794, discussed above, is directed toward the application of the present invention for tampon applicators either made of, or coated with, PVOH. This patent illustrates that tampon applicators treated with infrared treatment demonstrate substantially improved performance in comparison with the conventional, non-IR treated PVOH applicators. A home use test of 100 respondents was performed. Specifically, tampons having (1) PVOH barrels infrared treated as set forth above (with untreated cardboard plungers); and (2) untreated applicators having barrels and plungers of traditional polyethylene were tested.

| Attribute | # Preferring IR Treated PVOH | # Preferring Untreated Polyethylene | No Preference | Preference Ratio |
|---|---|---|---|---|
| Easy to insert | 32 | 29 | 39 | +1.1 |
| Comfortable to Insert | 29 | 25 | 46 | +1.1 |
| Easy to Eject From Applicator | 32 | 29 | 45 | +1.1 |
| Easy to Grip | 25 | 22 | 53 | +1.1 |

-continued

| Attribute | # Preferring IR Treated PVOH | # Preferring Untreated Polyethylene | No Preference | Preference Ratio |
|---|---|---|---|---|
| Overall Comfort | 28 | 20 | 52 | +1.2 |
| Smoothness of Applicator | 27 | 23 | 35 | +1.1 |
| The applicator | 38 | 38 | 24 | 1.0 |

A similar study was conducted comparing untreated PVOH applicators to traditional, untreated polyethylene applicators. All applicators were the same in size, shape, dimensions and fingergrips. The results below show that consumers clearly preferred the untreated polyethylene applicators to untreated PVOH applicators.

| Attribute | # Preferring Untreated PVOH | # Preferring Untreated Polyethylene | No Preference | Preference Ratio |
|---|---|---|---|---|
| Easy to insert | 13 | 43 | 28 | −2.1 |
| Comfortable to Insert | 14 | 42 | 28 | −2.0 |
| Easy to Eject From Applicator | 11 | 38 | 35 | −1.9 |
| Easy to Grip | 20 | 15 | 49 | +1.1 |
| Overall Comfort | 8 | 22 | 54 | −1.4 |
| Smoothness of Applicator | 8 | 43 | 33 | −2.4 |
| The applicator | 26 | 40 | 18 | −1.4 |

In summary, the results of these two tests show consumers clearly prefer the infrared treated PVOH (as compared to untreated polyethylene applicators) over untreated PVOH applicators. When comparing the preference ratios derived from the first experiment with infrared treated PVOH applicators (center column, below) versus untreated PVOH applicators the difference is obvious. This demonstrates the dramatic difference in product acceptability that is conferred by the infrared treatment of the present invention.

|  | Preference Ratio IR Treated PVOH | Preference Ratio Untreated PVOH |
|---|---|---|
| Comfortable to insert | +1.1 | −2.0 |
| Easy to insert | +1.1 | −2.1 |
| Easy to eject | +1.1 | −1.9 |
| Easy to grip | +1.1 | +1.1 |
| Smoothness of applicator | +1.1 | −2.4 |
| The applicator | +1.0 | −1.4 |
| Overall comfort | +1.2 | −1.4 |

Accordingly, the IR treated PVOH applicator has similar consumer acceptance ratings to the traditional polyethylene applicator, even before taking into account the consumer preference for flushable and biodegradable applicators. This is a substantial improvement over the results for the untreated PVOH applicator. Furthermore, the IR treated PVOH may have scored even better with a treated PVOH plunger instead of the cardboard plunger used in the test.

The consumer testing results set forth above demonstrate that the advantages of treating with infrared heat tampon applicators made from, or coated with, water-soluble polymers. It is believed by the applicants that the present invention is as effective with the polymer resins disclosed herein as has been proven with the consumer test studies conducted with PVOH.

Thus, it will be obvious to one of ordinary skill in the art that the foregoing description and drawings are merely illustrative of certain preferred embodiments of the present invention, and that various obvious modifications can be made to these embodiments in accordance with the spirit and scope of the appended claims.

What is claimed is:

1. A tampon applicator comprising:
 a barrel having an outer surface and a first end, said barrel being made of a water dispersible material; and
 a plunger adapted to be telescopically mounted in the first end of said barrel,
  wherein said outer surface of said barrel is treated by infrared radiation to minimize surface stickiness on initial contact with moisture.

2. The tampon applicator of claim 1, wherein said water dispersible material is selected from the group consisting of poly(b-hydroxy butyrate), poly(b-hydroxy butyrate)-co-(b-hydroxy valerate), poly(hydroxy acids), aliphatic polyesters, polycaprolactone, starch, cellulose acetate and cellulose diacetate.

3. The tampon applicator of claim 1, wherein said plunger is made of a material selected from the group consisting of a water dispersible polymer and cardboard, and said plunger is treated by infrared radiation to minimize surface stickiness on initial contact with moisture.

4. The tampon applicator of claim 3, wherein said water dispersible polymer is selected from the group consisting of poly(b-hydroxy butyrate), poly(b-hydroxy butyrate)-co-(b-hydroxy valerate), poly(hydroxy acids), aliphatic polyesters, polycaprolactone, starch, cellulose acetate and cellulose diacetate.

5. The tampon applicator of claim 1, wherein said plunger has an outer surface that is coated with a material comprising a water dispersible polymer.

6. The tampon applicator of claim 5, wherein said water dispersible polymer is selected from the group consisting of poly(b-hydroxy butyrate), poly(b-hydroxy butyrate)-co-(b-hydroxy valerate), poly(hydroxy acids), aliphatic polyesters, polycarpolactone, starch, cellulose acetate and cellulose diacetate.

7. The tampon applicator of claim 1, wherein said infrared radiation is generated by a radiant heater.

8. The tampon applicator of claim 1, wherein said infrared radiation comprises exposing said barrel to a source of infrared radiation having a temperature of about 700° F. to about 2500° F. for about 5 to about 60 seconds.

9. A tampon applicator comprising:
 a barrel having an outer surface and a first end, the outer surface of said barrel being coated with a water dispersible material; and
 a plunger telescopically mounted in the first end of said barrel,
  wherein said outer surface is treated by infrared radiation to minimize surface stickiness on initial contact with moisture.

10. The tampon applicator of claim 9, wherein said water dispersible material is selected from the group consisting of poly(b-hydroxy butyrate), poly(b-hydroxy butyrate)-co-(b-hydroxy valerate), poly(hydroxy acids), aliphatic polyesters, polycaprolactone, starch, cellulose acetate and cellulose diacetate.

11. The tampon applicator of claim 9, wherein said infrared radiation is generated by a radiant heater.

12. The tampon applicator of claim 9, wherein said infrared radiation comprises exposing said barrel to a source of infrared radiation having a temperature of about 700° F. to about 2500° F. for about 5 to about 60 seconds.

13. The tampon applicator of claim 9, wherein said plunger further comprises an outer surface, said outer surface of said plunger being coated with a coating material comprising said water dispersible material, and wherein said outer surface of said plunger is treated with infrared radiation after said outer surface of said plunger has been coated with said coating material.

14. The tampon applicator of claim 9, wherein said water dispersible material is selected from the group consisting of poly(b-hydroxy butyrate), poly(b-hydroxy butyrate)-co-(b-hydroxy valerate), poly(hydroxy acids), aliphatic polyesters, polycaprolactone, starch, cellulose acetate and cellulose diacetate.

15. A tampon applicator comprising:
   a barrel having an outer surface and a first end, said barrel being made of a water dispersible material; and
   a plunger telescopically mounted in the first end of said barrel, said plunger having an outer surface, said outer surface of said plungers being coated with a coating material comprising said water dispersible material, wherein said barrel and said plunger are exposed to infrared radiation prior to said tampon applicator being used, to minimize surface stickiness of said tampon applicator on initial contact with moisture.

16. The tampon applicator of claim 15, wherein said water dispersible material is selected from the group consisting of poly(b-hydroxy butyrate), poly(b-hydroxy butyrate)-co-(b-hydroxy valerate), poly(hydroxy acids), aliphatic polyesters, polycaprolactone, starch, cellulose acetate and cellulose diacetate.

17. A method for treating a tampon applicator barrel comprising the step of:
   subjecting a water dispersible outer surface of said barrel to a source of infrared radiation.

18. The method of claim 17, wherein said barrel is subjected to said source of infrared radiation from about 5 to about 60 seconds.

19. The method of claim 17, wherein said source of infrared radiation is at a temperature of about 700° F. to about 2500° F.

20. A method for treating a tampon applicator having a barrel and a plunger, comprising:
   subjecting said barrel and said plunger to a source of infrared radiation.

21. The method of claim 20, wherein said barrel is subjected to said source of infrared radiation from about 5 to about 60 seconds.

22. The method of claim 20, wherein said source of infrared radiation is at a temperature of about 700° F. to about 2500° F.

* * * * *